US011906492B2

(12) United States Patent
Hong et al.

(10) Patent No.: US 11,906,492 B2
(45) Date of Patent: Feb. 20, 2024

(54) APPARATUS FOR QUANTITATIVELY ANALYZING OXYGEN GENERATED IN BATTERY MATERIAL

(71) Applicant: LG Chem, Ltd., Seoul (KR)

(72) Inventors: Sungwon Hong, Daejeon (KR); Kyungmee Lee, Daejeon (KR); Nak Hee Choi, Daejeon (KR); Jeong Ae Ahn, Daejeon (KR); Jin Il Kim, Daejeon (KR)

(73) Assignee: LG Energy Solution, Ltd. (KR)

( * ) Notice: Subject to any disclaimer, the term of this patent is extended or adjusted under 35 U.S.C. 154(b) by 1251 days.

(21) Appl. No.: 16/479,049

(22) PCT Filed: Jan. 24, 2018

(86) PCT No.: PCT/KR2018/001066
§ 371 (c)(1),
(2) Date: Jul. 18, 2019

(87) PCT Pub. No.: WO2019/027112
PCT Pub. Date: Feb. 7, 2019

(65) Prior Publication Data
US 2019/0369072 A1 Dec. 5, 2019

(30) Foreign Application Priority Data
Jul. 31, 2017 (KR) .......................... 10-2017-0096955

(51) Int. Cl.
*G01N 31/12* (2006.01)
*G01N 1/22* (2006.01)
(Continued)

(52) U.S. Cl.
CPC .............. *G01N 31/12* (2013.01); *G01N 1/22* (2013.01); *G01N 33/0013* (2013.01);
(Continued)

(58) Field of Classification Search
CPC ...... G01N 1/22; G01N 31/12; G01N 33/0013; H01M 10/4285
See application file for complete search history.

(56) References Cited

U.S. PATENT DOCUMENTS 5,268,302 A * 12/1993 Rounbehler ........... G01N 31/12
422/89
5,442,949 A 8/1995 Kinoshita et al.
(Continued)

FOREIGN PATENT DOCUMENTS

| CN | 1645095 A | 7/2005 |
| CN | 101107382 A | 1/2008 |

(Continued)

OTHER PUBLICATIONS

Chaochao, G. et al. "Determination on explosion limit of pyrolysis gas released by lithium-ion battery and its risk analysis", Journal of Safety Science and Technology, Sep. 2016, pp. 46-49, vol. 12, No. 9. (Providing English Translation of Abstract only).
(Continued)

*Primary Examiner* — Jennifer Wecker
(74) *Attorney, Agent, or Firm* — Lerner David LLP

(57) ABSTRACT

An apparatus for quantitatively analyzing gas, particularly oxygen, generated in a battery material, particularly a cathode material is provided. The apparatus contains a switching valve and a sampling loop in a pyrolyzer, thereby allowing an EGA method, which was used only for the qualitative analysis of gas generated from a solid sample, to be used for the quantitative analysis of gas generated at a specific temperature when heat is applied by the pyrolyzer in a battery material.

10 Claims, 4 Drawing Sheets

(51) Int. Cl.
*G01N 33/00* (2006.01)
*H01M 10/0525* (2010.01)
*H01M 10/42* (2006.01)
*H01M 10/48* (2006.01)

(52) U.S. Cl.
CPC ....... *H01M 10/0525* (2013.01); *H01M 10/42* (2013.01); *H01M 10/48* (2013.01)

(56) References Cited

U.S. PATENT DOCUMENTS

| | | | |
|---|---|---|---|
| 2003/0017611 A1 | 1/2003 | Vanatta | |
| 2007/0122716 A1 | 5/2007 | Seo et al. | |
| 2008/0160192 A1 | 7/2008 | Thebault et al. | |
| 2009/0121129 A1 | 5/2009 | Wang et al. | |
| 2009/0280414 A1 | 11/2009 | Koh et al. | |
| 2013/0151167 A1* | 6/2013 | Broughton | G16C 20/40 702/25 |
| 2013/0182400 A1 | 7/2013 | Hong | |
| 2014/0241394 A1* | 8/2014 | Olson | H01M 10/486 250/341.1 |
| 2018/0299414 A1 | 10/2018 | Jung et al. | |

FOREIGN PATENT DOCUMENTS

| | | |
|---|---|---|
| CN | 101317284 A | 12/2008 |
| CN | 101517813 A | 8/2009 |
| CN | 100569997 C | 12/2009 |
| CN | 101798689 A | 8/2010 |
| CN | 102304374 A | 1/2012 |
| CN | 103209542 A | 7/2013 |
| CN | 104830356 A | 8/2015 |
| CN | 105295965 A | 2/2016 |
| CN | 105300785 A | 2/2016 |
| EP | 1073505 A1 | 2/2001 |
| EP | 1774316 A2 | 4/2007 |
| EP | 2217903 A1 | 8/2010 |
| EP | 2963060 A2 | 1/2016 |
| JP | S57159159 U | 10/1982 |
| JP | H06308107 A | 11/1994 |
| JP | H9311128 A | 12/1997 |
| JP | 2006226746 A | 8/2006 |
| JP | 2007108021 A | 4/2007 |
| JP | 2010181187 A | 8/2010 |
| JP | 2017009539 A | 1/2017 |
| JP | 2018526635 A | 9/2018 |
| KR | 20120010884 A | 2/2012 |
| KR | 101490210 B1 | 2/2015 |
| KR | 20170041100 A | 4/2017 |
| WO | WO-9108466 A1 * | 6/1991 |
| WO | 2004090534 A1 | 10/2004 |
| WO | 2017061803 A1 | 4/2017 |

OTHER PUBLICATIONS

Chinese Search Report for Application No. 201880007554.0 dated Jun. 2, 2021, pp. 1-6.

Mingjie, Z. et al., "Thermal Stability of High Energy Density LiNi0.815Co0.15Al0.035O2/ Li4Ti5O12 Battery", High Voltage Engineering, Jul. 2017, pp. 2221-2228, vol. 43, No. 7, China Academic Journal. (Providing English Translation of Abstract only).

Mukoyama, I et al., "Lithium Battery Properties of LiNi0.5Mn1.5O4 Powders Synthesized by Internal Combustion Type Spray Pyrolysis Apparatus Using Gas Burner", Key Engineering Materials, Oct. 2007, pp. 191-194, Trans Tech Publications, Switzerland.

C.M. Huang et al., Parametric study of anodic microstructures to cell performance of planar solid oxide fuel cell using measured porous transport properties, Journal of Power Sources, Available online Oct. 2009, pp. 2260-2265, Elsevier B.V..

Frontier Lab, Multi-Shot Pyrolyzer; EGA/PY-3030D, 2013, pp. 1-7, Version 3.00, Frontier Laboratories.

Frontier Laboratories Ltd., Multi-functional Pyrolyzer Technical Note; Procedures for Acquiring Pyrograms in Air and Its Automation, Date not known, p. 1, Frontier Laboratories Ltd.

International Search Report for Application No. PCT/KR2018/001066 dated May 8, 2018, pp. 1-2.

Sung Hyup Lee, et al., Thermal studies of charged cathode material (LixCoO2) with temperature-programmed decomposition-mass spectrometry, Journal of Power Sources, Available online Mar. 2010, pp. 5049-5051, Elsevier B.V..

Quantum Analytics, Frontier Laboratories and Quantum Analytics, Seminar with Lab Sessions, Oct. 19 and 20, 2016, Aspen Research Corporation, Maple Grove, MN, 192 pages.

* cited by examiner

[FIG. 1]
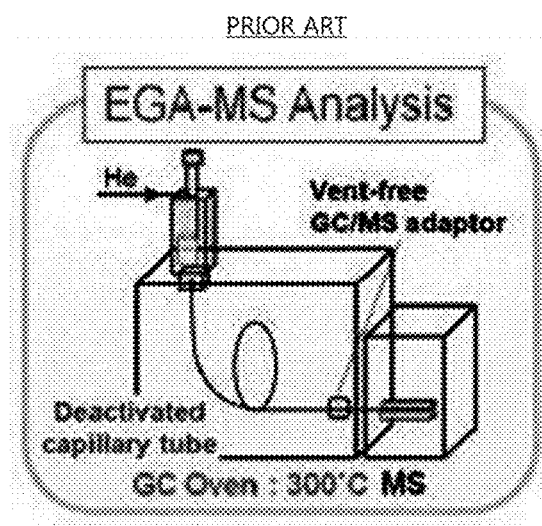
[FIG. 2]
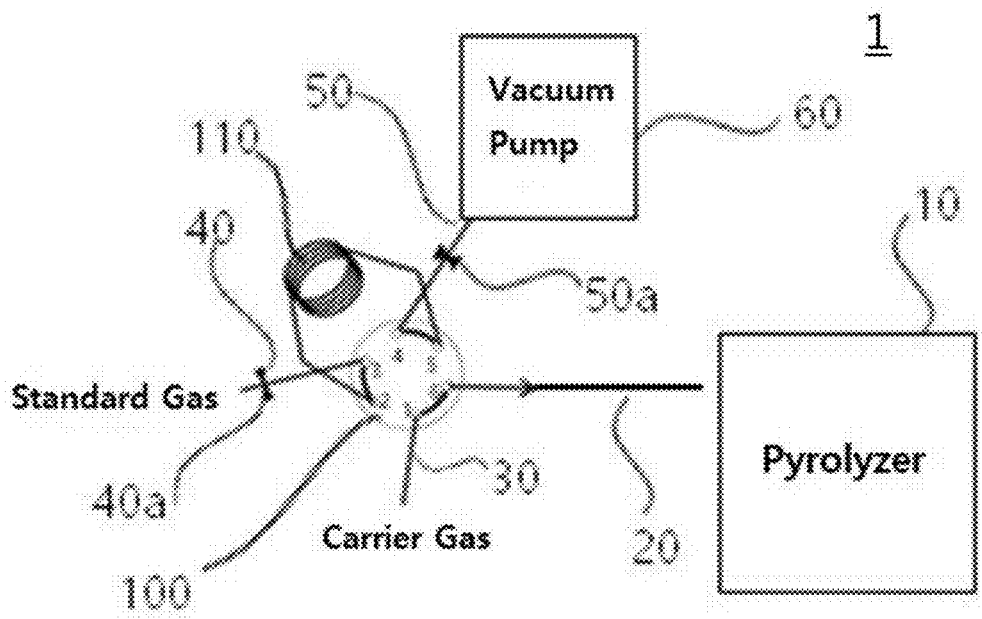

[FIG. 3a]
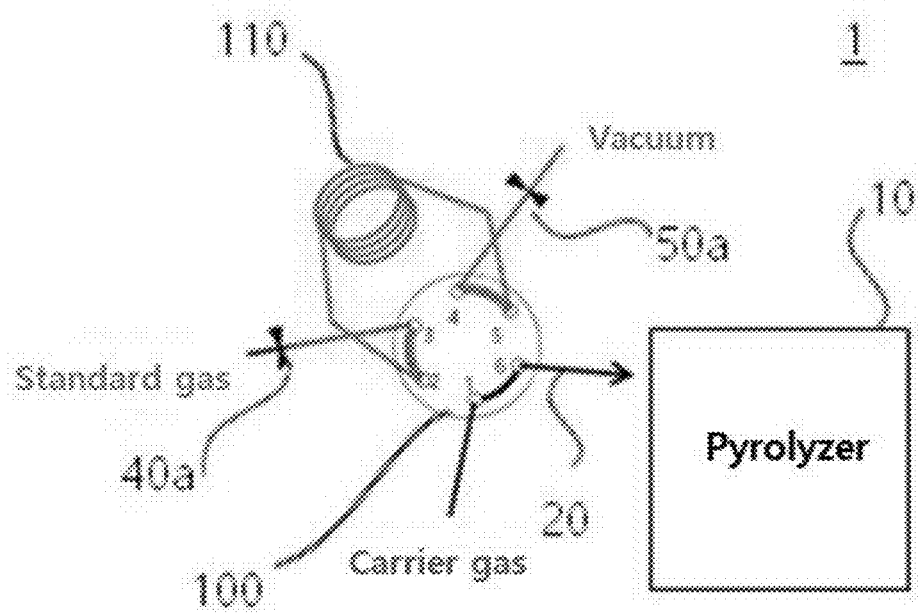
[FIG. 3b]
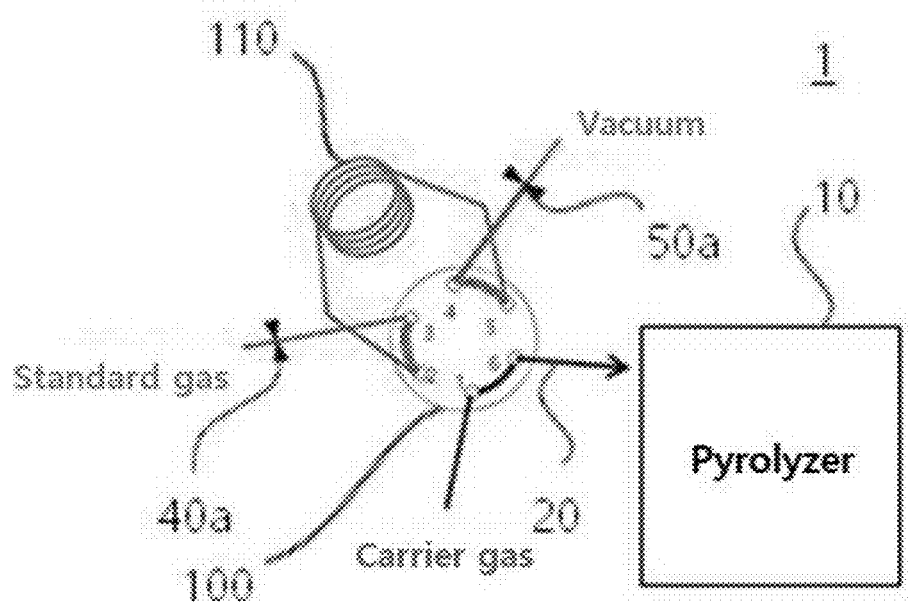

[FIG. 3c]
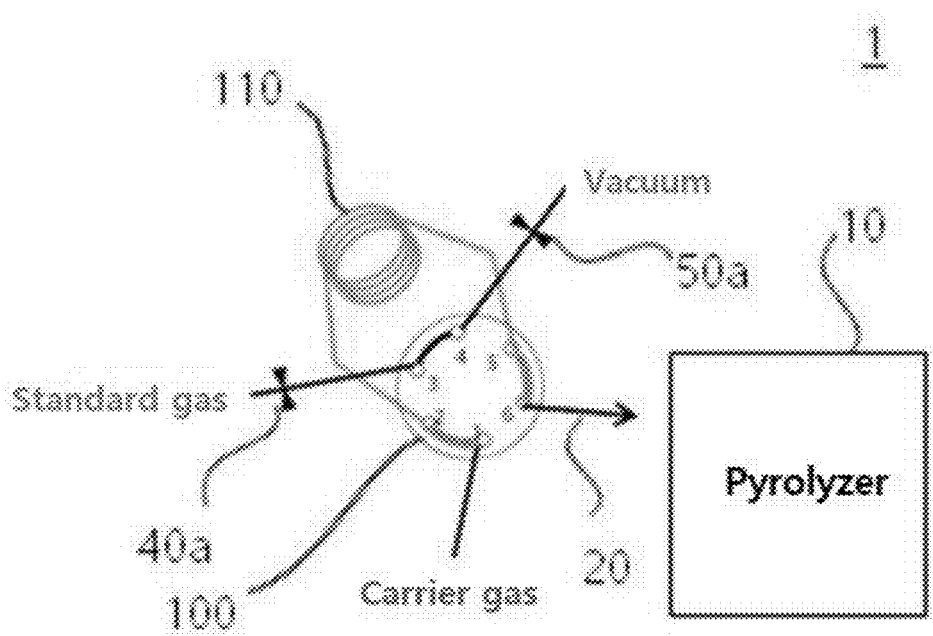
[FIG. 4]
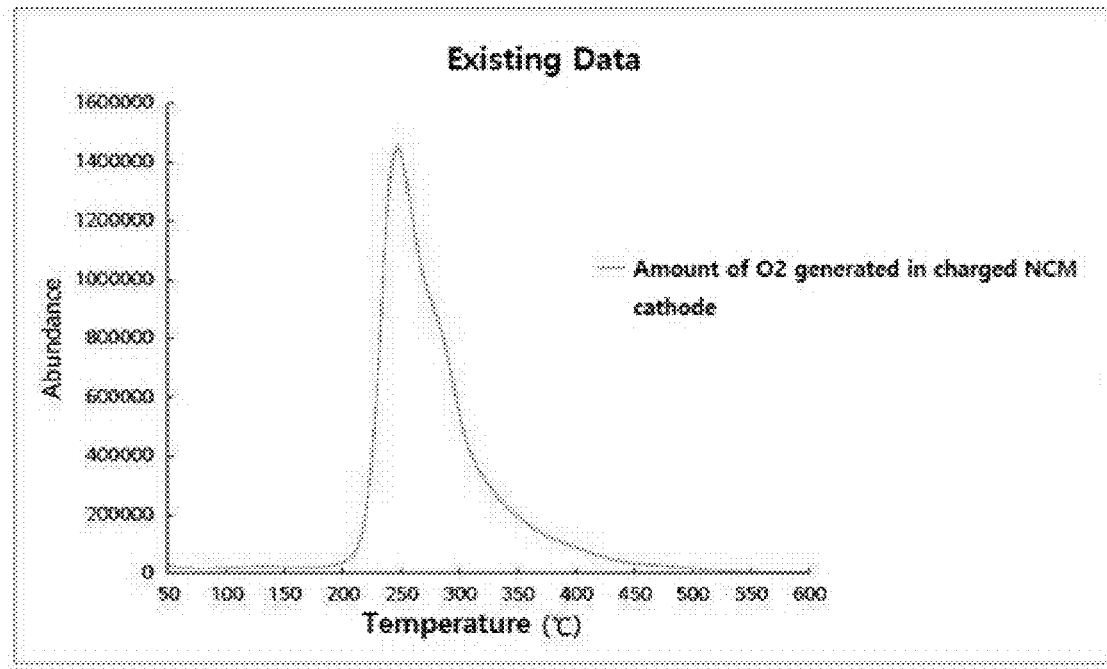

[FIG. 5]
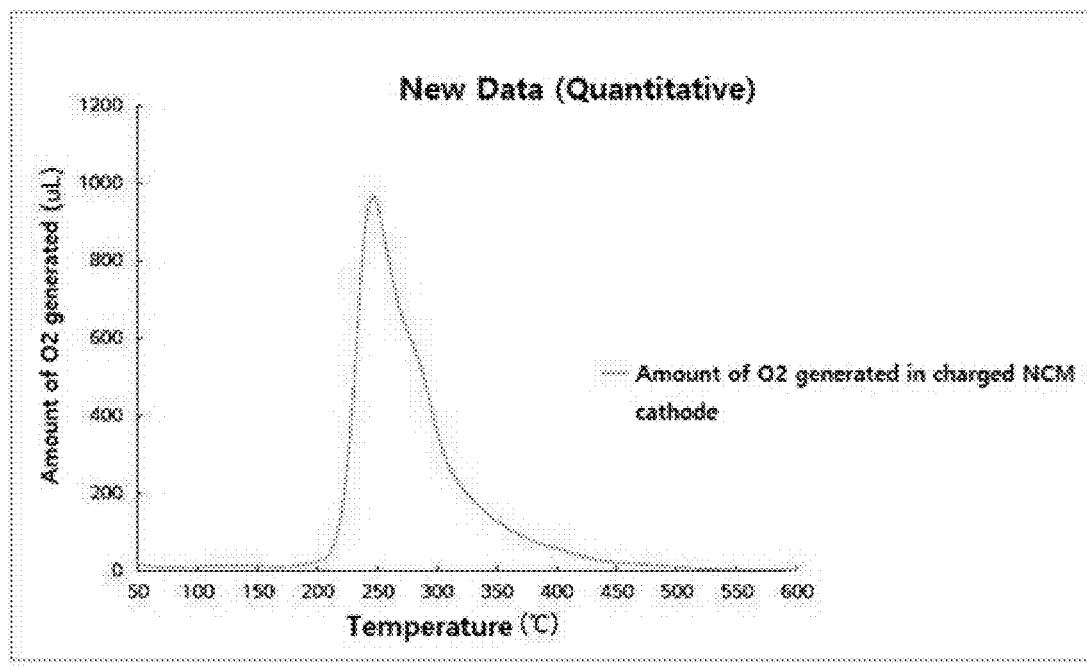
[FIG. 6]
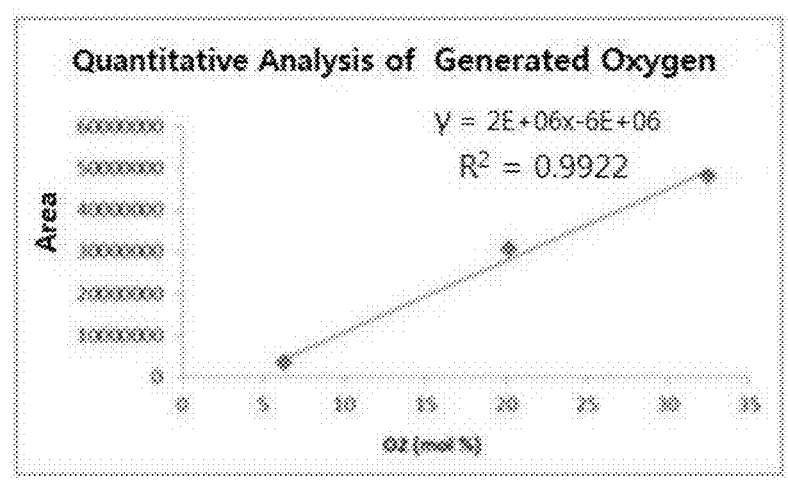

APPARATUS FOR QUANTITATIVELY ANALYZING OXYGEN GENERATED IN BATTERY MATERIAL

CROSS-REFERENCE TO RELATED APPLICATIONS

This application is a national phase entry under 35 U.S.C. § 371 of International Application No. PCT/KR2018/001066, filed Jan. 24, 2018, which claims priority to Korean Patent Application No. 10-2017-0096955, filed Jul. 31, 2017, the disclosures of which are incorporated herein by reference.

TECHNICAL FIELD

The present invention relates to an apparatus for quantitative analyses of gases, particularly oxygen, generated from cell materials.

BACKGROUND ART

Lithium ion batteries generate gas components such as hydrogen, oxygen, nitrogen, carbon monoxide, carbon dioxide, methane, ethane, ethylene, propane and the like during the operation thereof. These gases have been studied on the composition and content thereof in order to provide information for evaluating thermal and structural deformation of cells. The information may be usefully available for research and development of a cell material, optimization of cell manufacturing processes, identification of a cause of a cell failure, etc.

In order to quantitatively analyze gases generated inside the cells, it needs to collect them. Generally, the quantitative analyses of a solid sample and a gas generated from the solid sample have been made by using a method of evolved gas analysis mass spectroscopy (EGA-MS). However, the gases generated from the cell materials cannot be quantitatively analyzed by the conventional EGA method, and particularly oxygen can be analyzed only by injection of a standard gas. In documents [Journal of Power Sources 195 (2010) 5049-5051; Journal of Power Sources 195 (2011) 2260-2263], it is disclosed that hydrogen, water and carbon dioxide generated from a cathode material may be qualitatively analyzed by means of temperature-programmed decomposition-mass spectrometry (TPD-MS). However, it has no disclosure about quantitative analysis of gases by the EGA method.

Korean Patent Application Laying-open No. 10-2017-0041100 discloses a gas sample injection apparatus for quantitative analyses of gases generated from cells, which comprises an open/close valve (a switching valve) and a gas sampling loop. The apparatus applies a gas chromatography (GC) for analyses of the gases. Further, Korean Patent Application Laying-open No. 10-2012-0010884 discloses a quantitative analysis of acrylonitrile in an acrylonitrile-butadiene rubber composition by means of pyrolysis-GC. These patent documents have no disclosure about quantitative analyses of gases by the EGA method.

The present inventors have been endeavored to develop an apparatus for quantitative analyses of gases generated from cell materials by using the EGA method, and found that a port valve and a sampling loop are installed in the middle of a line for suppling a carrier gas into a pyrolyzer so as for a constant amount of standard gases to be injected into the pyrolyzer, thereby allowing the quantitative analysis of gases generated at a specific temperature when a cell material is applied with heat by the pyrolyzer.

DETAILED DESCRIPTION OF THE INVENTION

Technical Problem

The present invention is designed to provide an apparatus for quantitative analyses by EGA of gases generated at a specific temperature when heat is applied to cell materials by a pyrolyzer.

Technical Solution

In order to accomplish the above aspect, the present application provides an apparatus for quantitative analysis of gases, comprising:
  a pyrolyzer;
  a line for supplying a carrier gas into the pyrolyzer;
  a sampling loop for collecting a standard gas;
  a switching valve for injecting the standard gas collected in the sampling loop together with the carrier gas into the pyrolyzer; and
  a vacuum pump for vacuum-depressurizing the sampling loop,
  wherein the sampling loop is coupled to the switching valve, and the switching valve is coupled to the pyrolyzer through the line for supplying the carrier gas, and
  the standard gas is transferred in a constant amount into the pyrolyzer by action of the switching valve and the sampling loop for quantitative analyses of gases generated at a specific temperature when heat is applied to cell materials inside the pyrolyzer.

In one embodiment, the standard gas is collected in the vacuum-depressurized sampling loop and the switching valve is operated, thereby flowing the carrier gas through the sampling loop and injecting the carrier gas and the standard gas collected in the sampling loop through the line for supplying the carrier gas into the pyrolyzer.

In one embodiment, the pyrolyzer may be an evolved gas analyzer (EGA), or pyrolyzers being commercially available from Frontier Lab, CDS Analytical (www.cdsanalytical.com) or Japan Analytical Industry Co., Ltd. (http://www.ja-i.co.jp/english/index.html).

In one embodiment, the cell material is a cathode material comprising Li-metal oxide compounds ($LiMeO_2$), for example NCM, LCO, LMO, LNO and various combinations thereof.

In one embodiment, the gases generated from the cell material applied with heat of the pyrolyzer may be at least one selected from oxygen, carbon dioxide, carbon monoxide and water vapour.

In one embodiment, the carrier gas may be He, $N_2$ or Ar.

Advantageous Effects

According to the present invention, a port valve and a sampling loop are coupled to a pyrolyzer so that the standard gas is transferred in a constant amount into the pyrolyzer, thereby allowing the quantitative analyses of gases generated at a specific temperature when cell materials is applied with heat by the pyrolyzer, by using an EGA method which has been only applied in the qualitative analyses of gases generated from a solid sample.

BRIEF DESCRIPTION OF THE DRAWINGS

FIG. 1 schematically shows an EGA-MS apparatus according to the prior art.

FIG. 2 schematically shows an apparatus for quantitative analysis according to the present invention.

FIGS. 3a to 3c show the status of a switching valve and a sampling loop according to the operation of the apparatus of FIG. 2.

FIG. 4 shows measurement results of oxygen generated from an NCM-based cathode according to the prior art.

FIG. 5 shows the results of measuring the amount of oxygen generated from an NCM-based cathode by using the apparatus for quantitative analysis according to the present invention.

FIG. 6 shows a linear calibration curve for detection area of a standard gas (oxygen) to the molar ratio of oxygen.

BEST MODE

Hereinafter, the apparatus for quantitative analysis according to the present invention will be described in detail.

Prior to the description, it should be understood that the description proposed herein is just a preferable example for the purpose of illustrations only, not intended to limit the scope of the invention, so it should be understood that other equivalents and modifications could be made thereto without departing from the spirit and scope of the invention. Meanwhile, the description of the well-known functions or constructions may be omitted it it would obscure the subject matter of the present invention.

Also, the same reference numerals, unless otherwise stated, are used to denote the same or equivalent elements, components or parts illustrated in the drawings, and the repeated explanation thereof will be omitted. In addition, the size and shape of each element, component or part in the drawing may be shown in an enlarged or reduced scale for the sake of convenience.

The prior EGA cannot perform the quantitative analysis of gases generated from cell materials.

In contrast, the apparatus the present invention comprises a port valve and a sampling loop being installed in the middle of a line for suppling a carrier gas into a pyrolyzer so as for a constant amount of standard gases to be injected into the pyrolyzer, thereby allowing the quantitative analyses of gases generated at a specific temperature when cell materials is applied with heat by the pyrolyzer.

Specifically, the apparatus for quantitative analysis of gases according to the present invention comprises:
- a pyrolyzer;
- a line for supplying a carrier gas into the pyrolyzer;
- a sampling loop for collecting a standard gas;
- a switching valve for injecting the standard gas collected in the sampling loop together with the carrier gas into the pyrolyzer; and
- a vacuum pump for vacuum-depressurizing the sampling loop,
- wherein the sampling loop is coupled to the switching valve, and the switching valve is coupled to the pyrolyzer through the line for supplying the carrier gas, and the standard gas is transferred in a constant amount into the pyrolyzer by action of the switching valve and the sampling loop for quantitative analyses of gases generated at a specific temperature when heat is applied to cell materials inside the pyrolyzer.

In one embodiment, the standard gas is collected in the vacuum-depressurized sampling loop and the switching valve is operated, thereby flowing the carrier gas through the sampling loop and injecting the carrier gas and the standard gas collected in the sampling loop through the line for supplying the carrier gas into the pyrolyzer.

In one embodiment, the pyrolyzer may be an evolved gas analyzer (EGA), or pyrolyzers being commercially available from Frontier Lab, CDS Analytical (www.cdsanalytical.com) or Japan Analytical Industry Co., Ltd. (http://www.jai.co.jp/english/index.html).

In one embodiment, the cell material is a cathode material comprising Li-metal oxide compounds ($LiMeO_2$), for example NCM, LCO, LMO, LNO and various combinations thereof.

In one embodiment, the gases generated from the cell material applied with heat of the pyrolyzer may be at least one selected from oxygen, carbon dioxide, carbon monoxide and water vapor.

In one embodiment, the carrier gas may be He, $N_2$ or Ar.

EMBODIMENTS

Hereinafter, preferred embodiments of the present invention will be described in detail so that a person having ordinary skill in the art enables the present invention, however it is not intended to limit the scope of the present invention, and other equivalents and modifications could be made thereto.

FIG. 2 schematically shows an apparatus 1 for quantitative analysis according to one embodiment of the present invention. The quantitative analysis apparatus 1 comprises a pyrolyzer 10, a line 20 for supporting a carrier gas into the pyrolyzer 10, a switching valve 100 coupled to the front end of the one, a sampling loop 110 coupled to the switching valve 100, and a vacuum pump 60 for vacuum-depressurizing the sampling loop.

The pyrolyzer 10 may be an evolved gas analyzer (EGA), or pyrolyzers being commercially available from Frontier Lab, CDS Analytical (www.cdsanalytical.com) or Japan Analytical Industry Co., Ltd. (http://www.jai.co.jp/english/index.html). According to the present invention, it may also be implemented by coupling the sampling loop 110 and the switching valve 100 to the EGA, without a mass spectrometer (MS) or a gas chromatograph (GO). Further, it may be implemented by applying an instrument such as MS or GC, and IR (FT-IR, NIR), various gas sensor (e.g., $O_2$ sensor, $CO_2$ sensor, etc.), a laser analyzer (for analyzing oxygen) and the like (see http://www.hitouch.co.kr/productidetail02?seq=321&code=020301 for application of the $O_2$ sensor).

Meanwhile, the prior art has been applied only for qualitative analyses of gases generated from a sample on the pyrolysis of the sample as it is difficult to quantitatively inject a standard gas into the pyrolyzer. Basically, when the sample is pyrolyzed to generate gases, the gases are decomposed into a small gas molecule unit, which cannot be introduced into the pyrolyzer. For this reason, the present invention provides a valve system which can control the standard gas for the purpose of quantitative analyses of the gases.

Accordingly, the quantitative analysis apparatus 1 according to the present invention comprises the sampling loop 110 and the switching valve 100 coupled to the front end of the line 20 for supplying a carrier gas into the pyrolyzer 10, thereby allowing the quantitative analysis of the gases generated at a specific temperature when heat is applied to the sample inside the pyrolyzer 10.

First, a standard gas is injected into the pyrolyzer 10 by the sampling loop 110 and the switching valve 100 coupled to the front end of the line 20 for supplying a carrier gas into the pyrolyzer 10, while a calibration curve for the standard gas is obtained in the state that there is no sample in the the pyrolyzer 10. For example, FIG. 6 shows a linear calibration curve for detection area of a standard gas (oxygen) to the molar ratio of oxygen, which will be described below.

Then, a carrier gas is injected into the pyrolyzer 10 by the sampling loop 110 and the switching valve 100 coupled to the front end of the line 20 for supplying a carrier gas into the pyrolyzer 10, while a sample is subject to pyrolysis in the pyrolyzer 10 to generate gases and the amount of the gases generated from the sample may be calculated by using the calibration curve for the standard gas as obtained in the above.

Thus, the standard gas can be supplied in a constant amount into the pyrolyzer 10 by the sampling loop 110 and the switching valve 100, thereby quantifying the amount of oxygen among the gases generated from the sample inside the pyrolyzer 10.

The switching valve 100 may control the standard gas to be collected in the sampling loop 110, and it may control the standard gas to be injected in a constant amount into the pyrolyzer 10. The switching valve 100 is not particularly limited if it is used in the art. For example, a six-port valve, nine-port valve or ten-port valve may be used in one embodiment.

Referring to FIG. 2 according to one embodiment, the number of each port in a six-port valve 100 is assigned in convenience. The port numbers are assigned clockwise around port 1. The port 1 is connected to a gas-supplying line 30, ports 2 and 5 are connected to the sampling loop 110, port 3 is connected to a standard gas-supplying line 40, port 4 is connected to a vacuum pump 60 through the vacuum pump line 50, and port 6 is connected to the line 20 for supplying gases into the pyrolyzer. Although FIG. 2 illustrates a six-port valve 100 as an example, but the present invention is not limited thereto. For example, a plurality of valves may be used according to various embodiments of the present invention, and the configurations of connecting each components to any one among several ports of the switching valve 100 may be varied or modified according to the intended embodiments of the present invention.

The sampling loop 110 is not limited to its material and volume, but it may be made of materials with high strength to have no deformation of shape and volume during vacuum depressurizing, for example metal materials such as stainless steel, copper steel, carbon steel, aluminum steel and alloy steel, and polymer resins such as polyether ether ketone (PEEK) and polyimide. The volume of the sampling loop 110 should be properly controlled since it may affect the precision of analysis. For example, a volume of 1,000 μL (1 mL) or less, e.g., 50 μL, 250 μL or 500 μL may be used. Larger the sampling loop, lower the pressure of the standard gas. Smaller the sampling loop, higher the pressure of the standard gas. The amount of the standard gas filled in the sampling loop may be varied considering the amount of gases generated in cell materials.

The vacuum pump 60 is connected to the switching valve 100 and it is used in the vacuum-depressurizing of the sampling loop 110. As the vacuum pump 60, a rotary pump (a vacuum level of $10^{-2}$ mbar, 20 L/min) may be generally used. But the vacuum pump is not limited thereto, and various modifications may be made according to the intended embodiments of the present invention.

Also, the quantitative analysis apparatus 1 of the present invention may further comprise an operator (not shown) and a controller (not shown) for controlling the operation of the switching valve 100 and the open/close of the valves 40a and 50a in a manner as shown in FIGS. 3a to 3c. As the valves, solenoid valves or diaphragm valves may be used.

The apparatus of the present invention applies the coupling of the sampling loop 110 and the switching valve 100 to the pyrolyzer 10 for quantitative analysis of gases generated from the sample inside the pyrolyzer 10, and it is a novel concept which has not applied in the conventional analysis method by pyrolysis.

FIGS. 3a to 3c show the status of a switching valve 100 and a sampling loop 110 according to the operation of the quantitative analysis apparatus 1 of FIG. 2. For convenience, some components and reference numerals which are the same as those in FIG. 2 are omitted.

FIG. 3a shows a state in which the sampling loop 110 is subject to vacuum-depressurizing. The valve 40a is provided in the standard gas-supplying line 40 connected to the port 3 of the switching valve 100 and it is closed. The valve 50a is provided in the vacuum pump line 50 connecting between the port 4 of the switching valve 100 and the vacuum pump 60 and it is opened. Thereby, as shown in FIG. 3a, the vacuum pump line 50 connected to the port 4, a connecting portion of the port 2 and the port 3, a connecting portion of the port 4 and the port 5, and a sampling loop 110 connected to the port 2 and the port 5 are vacuum-depressurized by the vacuum pump 60. Meanwhile, a carrier gas is constantly supplied into the pyrolyzer 10 in order of the line 30 for supplying a carrier gas, the port 1, the port 6 and the line 20 since the port 1 and the port 6 of the switching valve 100 are connected to each other.

FIG. 3b is a subsequent state of FIG. 3a and shows a state in which the vacuum-depressurized sampling loop 110 is filled with the standard gas. The valve 40a, which is provided in the standard gas-supplying line 40 connected to the port 3 of the switching valve 100, is open. The valve 50a, which is provided in the vacuum pump line 50 connecting between the port 4 of the switching valve 100 and the vacuum pump 60, is closed. Thereby, as shown in FIG. 3b, a connecting portion of the port 2 and the port 3, a connecting portion of the port 4 and the port 5, a sampling loop 110 connected to the port 2 and the port 5, and a portion between the valve 50a and the port 4 in the vacuum pump line 50 are filled with the standard gas through the standard gas-supplying line 40 connected to the port 3. Meanwhile, a carrier gas is also constantly supplied into the pyrolyzer 10 in order of the port 1, the port 6 and the line 20 since the port 1 and the port 6 of the switching valve 100 are connected to each other.

FIG. 3c is a subsequent state of FIG. 3b and shows a state in which the switching valve 100 is operated to transfer the standard gas in the sampling loop 110 by action of the carrier gas into the pyrolyzer 10. By the operation of the switching valve 100, the connecting state between each port is switched from the state of FIG. 3b to the state of FIG. 3c. Thereby, the carrier gas moves to the port 1, the port 2, the sampling loop 110, the port 5 and port 6, in order, as shown in FIG. 3c, not directly moving from port 1 to port 6. At this time, the carrier gas is supplied, together with the standard gas filled in the sampling loop 110 in FIG. 3b, through the line 20 into the pyrolyzer 10. The same procedure of filling a standard gas with different oxygen concentration in the sampling loop is repeated to calculate a calibration curve for the standard gas. FIG. 6 shows a linear calibration curve for detection area of oxygen as a standard gas to the molar ratio of oxygen.

After calculating the calibration curve for the standard gas, the switching valve 100 operates to further perform the vacuum depressurizing of the sampling loop 110 as shown in FIG. 3a. Then, the switching valve 100 operates to move the carrier gas from the port 1, the port 2, the vacuum depressurized sampling loop 110, the port 5 and the port 6, in order, as shown in FIG. 3c, from which the carrier gas is supplied through the line 20 into the pyrolyzer 10. At this time, cell materials in the pyrolyzer 10 is subject to pyrolysis to generate gases, among which the target gas (e.g., oxygen gas) is detected for measurement of its area. The area of the detected gas can be quantitatively analyzed by using the calibration curve of the standard gas.

EXAMPLES

1. Prior Art

The conventional EGA has been made by using an EGA-MS apparatus as shown in FIG. 1. Specifically, it is for qualitative analyses of gases generated from a solid sample by relatively comparison of the amounts of the generated gases relative to a reference sample. However, this cannot be applied in the quantitative analysis of gases generated from cell materials.

2. Quantitative Analyses of Gases Generated from Cell Materials by Using the Apparatus of the Present Invention The apparatus of the present invention as shown in FIG. 2 was used for quantitative analysis of oxygen generated from cell materials. Specifically, the amount of oxygen was analyzed as follows.

A carrier gas was supplied at 1 mL/min by using an MFC (mass flow controller). The sampling loop was evacuated in a vacuum of $1 \times 10^{-2}$ torr or less by using a rotary pump (commercially available from EDWARDS), and filled with 99.9 mol (%) of the standard gas to be 50 torr. At this time, the concentration of the standard gas was 99.9 mol %×50 torr I 760 torr=6.572 mol %. 6.572 mol % of oxygen filled in the sampling loop was injected together with the carrier gas into the pyrolyzer, and the amount thereof was accurately analyzed by using an analyzer (mass spectrometer). From the analyzer, the molecular ion value for oxygen, m/z=32 was extracted and the area thereof was calculated. This procedure was repeated for standard gases with different concentrations to obtain calibration curves according to the area values and concentrations.

A lithium ion battery comprising an NCM-based cathode was charged and decomposed in a glove box of an Ar (argon) environment. The cathode was washed with DMC, and dried under reduced pressure for complete removal of the DMC.

The dried cathode was precisely taken in an amount of 5 to 10 mg, and introduced into a pyrolyzer and subject to pyrolysis to analyze the amount of oxygen generated therefrom. Then, the molecular ion value for oxygen, m/z=32 was extracted and the area thereof was calculated. The calculated area value was applied to the calibration curve for the standard gas to determine the precise amount of oxygen.

FIG. 5 shows a graph indicating the amount of generated oxygen according to the temperature. FIG. 6 shows a result of quantitative analysis of the amount of generated oxygen by using a calibration curve for standard gas.

As confirmed in the above, the apparatus of the present invention comprises a port valve and a sampling loop coupled to the pyrolyzer, thereby allowing the quantitative analysis of oxygen generated in the cathode.

While the present invention has been particularly shown and described with reference to figures and embodiments thereof, it will be understood by those of ordinary skill in the art that the scope of the present invention is not limited thereby and that various changes and modifications may be made therein. Therefore, the actual scope of the present invention will be defined by the appended claims and their equivalents.

What is claimed is:

1. An apparatus for quantitative analysis of a gas sample, comprising:
    a pyrolyzer;
    a line for supplying a carrier gas into the pyrolyzer;
    a sampling loop for collecting a standard gas;
    a switching valve for injecting the standard gas collected in the sampling loop together with the carrier gas into the pyrolyzer; and
    a vacuum pump configured to vacuum depressurize the sampling loop,
    wherein the sampling loop is directly coupled to the switching valve, and the switching valve is directly coupled to the pyrolyzer through the line for supplying the carrier gas, and
    wherein the sampling loop and the switching valve are configured to inject the standard gas into the pyrolyzer at a constant amount.

2. The apparatus for quantitative analysis of a gas sample according to claim 1, wherein the standard gas is collected in the sampling loop that is vacuum depressurized and the carrier gas flows through the sampling loop as the switching valve is operated and the carrier gas and the standard gas are injected into the pyrolyzer.

3. The apparatus for quantitative analysis of a gas sample according to claim 1, wherein the switching valve is operated after the sampling loop is subject to vacuum-depressurizing by the vacuum pump, thereby injecting the carrier gas through the sampling loop that is a vacuum-depressurized and into the pyrolyzer wherein the pyrolyzer is configured to detect an amount of gases generated from a cell material inside the pyrolyzer.

4. The apparatus for quantitative analysis of a gas sample according to claim 1, wherein the pyrolyzer is an evolved gas analyzer (EGA).

5. The apparatus for quantitative analysis of a gas sample according to claim 1, wherein the gas sample comprises a gas generated when heat is applied to a cell material by the pyrolyzer.

6. The apparatus for quantitative analysis of a gas sample according to claim 5, wherein the cell material is a cathode material comprising Li-metal oxide compounds ($LiMeO_2$).

7. The apparatus for quantitative analysis of a gas sample according to claim 5, wherein the gases generated from the cell material applied with heat of the pyrolyzer is at least one selected from oxygen, carbon dioxide, carbon monoxide and water vapor.

8. The apparatus for quantitative analysis of a gas sample according to claim 1, wherein the carrier gas is He, $N_2$ or Ar.

9. A method for quantitative analysis of a gas sample by using the apparatus for quantitative analysis of a gas sample according to claim 1, comprising:
    collecting the standard gas in the sampling loop that is vacuum depressurized;
    operating the switching valve for flowing carrier gas through the sampling loop; and
    injecting the carrier gas and the standard gas into the pyrolyzer.

10. A method for quantitative analysis of a gas sample by using the apparatus for quantitative analysis of a gas sample according to claim 1, comprising:

operating the switching valve after the sampling loop is subject to vacuum-depressurizing by the vacuum pump;
injecting the carrier gas through the sampling loop that is vacuum-depressurized and into the pyrolyzer; and
detecting an amount of gases generated from a cell material inside the pyrolyzer.

* * * * *